United States Patent [19]

Bornengo et al.

[11] Patent Number: 4,851,037

[45] Date of Patent: Jul. 25, 1989

[54] COLLECTING AGENTS FOR THE SELECTIVE FLOTATION OF LEAD AND ZINC ORES AND A PROCESS FOR PREPARING THE SAME

[75] Inventors: Giorgio Bornengo, Novara; Filippo M. Carlini, Vicenza; Anna Marabini, Frascati; Vittorio Alesse, Rome, all of Italy

[73] Assignee: Consiglio Nazionale Delle Ricerche, Rome, Italy

[21] Appl. No.: 106,905

[22] Filed: Oct. 9, 1987

Related U.S. Application Data

[62] Division of Ser. No. 818,306, Jan. 13, 1986, abandoned.

[51] Int. Cl.[4] .......................... B03D 1/14; C22B 1/00; C07C 103/22

[52] U.S. Cl. .......................................... 75/2; 209/166; 252/61; 558/412; 564/162; 564/440

[58] Field of Search ................ 564/162, 440; 558/412; 252/61; 75/2; 209/166

[56] References Cited

U.S. PATENT DOCUMENTS

| | | | |
|---|---|---|---|
| 2,034,459 | 3/1936 | Cole | 564/440 |
| 2,776,749 | 1/1957 | Powell et al. | 209/166 |
| 3,006,471 | 10/1961 | Luttinger | 209/166 |
| 3,188,322 | 6/1965 | Yale et al. | 564/440 |
| 3,585,143 | 6/1971 | Muzycko et al. | 564/440 |
| 4,735,711 | 4/1988 | Klimpel et al. | 252/61 |

*Primary Examiner*—Glennon H. Hollrah
*Assistant Examiner*—Raymond Covington
*Attorney, Agent, or Firm*—Pollock, Vande Sande & Priddy

[57] ABSTRACT

Ionic organic collecting agents for the selective flotation of lead and zinc ores, said agents having the following general formula

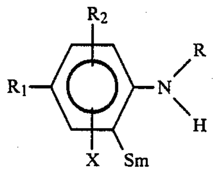

I wherein the symbols employed have the meaning given below:

R represents H, $CH_3$, $C_2H_5$, or an alkoxyalkyl group, $R_1$ and $R_2$, which can be the same or different, represent H, a linear or a branched alkyl group, an alkoxyalkyl group or a hydroxyalkyl group containing up to 12 carbon atoms;

X represents H, Cl, Br, I, F, CN, $CONH_2$, $NO_2$;

m represents H, Na, K, Li, Cs;

as well as a process for the production of said collecting agents.

9 Claims, No Drawings

COLLECTING AGENTS FOR THE SELECTIVE FLOTATION OF LEAD AND ZINC ORES AND A PROCESS FOR PREPARING THE SAME

This application is a division of application Ser. No. 818,306, filed Jan. 13, 1986 now abandoned.

DISCLOSURE OF THE INVENTION

This invention relates to ionic organic collecting agents for the selective flotation of lead and zinc metal ores as well as to a process for the production of said collecting agents. As is well known in the prior art, all collecting agents employed or known up to the present time can be classified into two types: the ionic and the non-ionic collecting agents. The employment of neutral or oily collecting agents is limited generally to the flotation of nonpolar ores on which said agents are adsorbed by Van der Waals forces or by forces of a physical type, whereas the ionizable chemical collecting agents are employed for all other ore species on the surfaces of which they become adsorbed by bonds of an essentially chemical type. Though chemical adsorption is more selective than physical adsorption, it is to be observed that ionic collecting agents too are active to some definite ore classes (for instance the sulfides) and that said agents have no selectivity for the single ore.

Thus, in order to separate by flotation a given mineral from a mixture of minerals belonging to a class or kind of the same type, it is necessary to employ modifying compounds which, by acting in a suitable way, make the action of the collecting agent more specific.

However, the employment of such reagents often gives remarkable drawbacks and quite often brings about undesired results, especially in the case of minerals of complex chemical compositions, whose surface properties are not known sufficiently.

From such considerations the importance stems of making available collecting agents capable of selectively bonding to some definite minerals. This is made possible by the presence in the structure of said collecting agents of active groups showing a particular affinity to some definite cations which are found typically on the surface of said mineral.

By supposing the existence of a close correlation between phenomena occurring in the solution which involve real chemical reactions and phenomena occurring on surfaces, the possibility was investigated in the present invention of employing for the flotation process some ionic organic reagents which, at the present time, are an object of an ever increasing interest in analytical chemistry because of their characteristics of specifical action or of high selective action to some definite inorganic ions, and in particular to metallic ions.

Such reagents are known in analytical chemistry as "chelating agents" and they are organic compounds capable of linking to some definite metal ions at a number of sites of their molecules, thus forming one or more rings which give the compound a very high stability.

Only general and poor information is available about the employment of such reagents in flotation processes in the old technical literature. For instance, Gutzeit employed chelating agents in the anionic flotation of iron oxidized minerals as sequestering agents for heavy metal ions in order to prevent quartz from floating. On the basis of such premise, the present invention solves the problem of obtaining advantageously the hydrophobic character of the ore particles to be floated by making functional with hydrocarbon radicals some classes of organic chelating agents to be employed as flotation collecting agents.

Accordingly, it is an object of the present invention to supply a class of ionic organic collecting agents which are selective for the flotation of lead and zinc ores, said agents being of the following general formula:

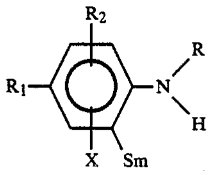

I wherein the symbols used have the following meanings:

R represents H, $CH_3$, $C_2H_5$, an alkoxyalkyl group, $R_1$ and $R_2$, which can be the same or different, represent H, a linear or a branched alkyl group, an alkoxyalkyl or hydroxyalkyl group containing up to 12 carbon atoms, X represents H, Cl, Br, I, F, CN, $CONH_2$, $NO_2$, m is H, Na, K, Li, Cs.

The collecting agents which are the object of the present invention are selective for the flotation of lead and zinc ores, and more specifically they can be employed for flotation of galena, sulfurized cerussite, zinc blende, smithsonite and hemimorphite.

Up to the present time no report can be found about the class of the selective flotation collecting agents of the general formula I which are the object of the present finding, though some compounds are known which are ortho-aminothiophenol derivatives, said compounds being of a limited application as analytical reagents or as diazotizable bases for dyestuffs. Moreover, no information is available about the employment of compounds having the general formula I in the field of selective collecting agents for the flotation of lead and zinc ores.

Accordingly those who are skilled in the art are not likely to find the way to synthesize ionic collecting agents having remarkable selective flotation properties for lead and zinc ores such as the collecting agents of formula I obtained according to the present invention.

This as well as other objects can be obtained according to the present invention by means of the compounds of the general formula I. Said compounds are obtained according to the present invention through a process wherein an amine of the formula:

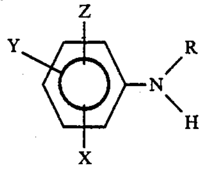

II wherein:

R and X have the same meanings as given above, Y and Z, which are the same or different, represent H, —OH, —CHO, is reacted with a linear or branched alkyl halide so as to obtain the compound of the formula

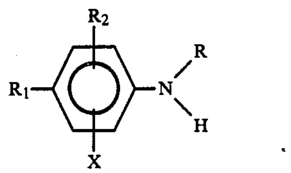

III wherein X, R, $R_1$ and $R_2$ have the same meanings as given above, and the —Sm function is introduced into the aromatic ring at the "ortho" with respect to the amine group, the meaning of m being already given above.

It is to be observed that the various flotation collecting agents taken into consideration in the procedure of the present invention, are only those which are capable of forming water-insoluble compounds with metals, the metal ion in such compounds being linked to the organic molecule both through an ionic bond and through a donor bond; the association of the metal with the collecting agent occurs so that the coordination number and the metal charge are balanced exactly by the sum respectively of the donor groups and of the charges of the collecting agent ions with which said metal combines.

Thus according to the present invention it has been found out that the properties of the reagents in question are better than those of the commonly used collecting reagents, and that the reagents of the present invention show particularly different from the common reagents as regards their high specific properties towards metal ions as well as because of the structural differences in their nonpolar part.

Accordingly, the present invention allows the possibility of obtaining organic ionic collecting agents for the selective flotation of metal ores, especially of minerals of quite a complex structure, for instance of lead and zinc ores which give difficulties in the selective flotation processes, said collecting agets acting through the co-action of the same. Such collecting agents were shown to be of a large practical and economical importance.

More particularly, the selection of a collecting agent for each type of ore was determined by the capability of said agent to form chelation compounds of the insoluble type with cations that make part of the ore composition.

In order to obtain data inherent to the present invention according to the directions of analytical chemistry techniques, experimetal tests were performed to find the pH values and the collecting agent concentration at which the flotation process of said lead and zinc ores is carried out with a satisfying result.

Next the variations were investigated for each ore of matter recovered in the full range of pH values keeping fixed at given values the concentrations of the collecting agent, with respect to the values obtained in the experimental tests mentioned beforehand.

The optimal pH values was thus found out exactly for the flotation process.

It was also possible to find the flotation conditions for all ores at which the recovery was almost full in the presence of the collecting agent.

Such conditions are analogous to those in which the quantitative precipitation of the cations in question is performed according to analytical chemistry techniques.

While all that shows again the possibility of transferring the solution reaction principles to phenomena occurring on surfaces, it also confirms the validity of the hypothesis on which the procedure according to the present invention is based.

Again according to the present invention it was also found that, when a hydrophobic linear or branched alkyl chain, an alkoxyl or a hydroxyalkyl group containing up to 12 carbon atoms are introduced into an aromatic molecule containing two chelating functions

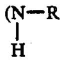 and

Sm), in the "ortho" position with respect to the other substituting groups, said molecule has in itself the properties that are separately supplied by the chelating agents and the oil.

The present invention will be disclosed in the following more exactly by means of employment and preparation examples of the collecting agents, said examples being given for illustrative and not for limitative purposes of the invention.

EXAMPLES

Example 1

The preparation of a flotation collecting agent through Hertz's synthesis 16.5 parts of parabutoxyaniline are dissolved into 150 parts of acetic acid glacial. 66.7 parts of sulfur monochloride ($S_2Cl_2$) are collected in 30 minutes at room temperature. After stirring for 1 hr the mixture is gradually heated up to a temperature of 80° C., keeping that temperature till hydrogen fluoride vapors evolution disappears. Without stopping stirring the mixture it is cooled with an ice-water bath and then filtered, the precipitate being washed on the filter with 60 parts of ethyl ether. After drying at 40° C., 22 parts are obtained of a yellow powder of a cyclic salt (4-butoxy-benzodithiazole chloride).

The product dissolved in 50 parts of water is first hydrolized by heating to 40° C., then by adding to the solution 8 parts of 100% NaOH and heating up to 60° C. for 2 hours. The reaction product (4-butoxy-ortho-mercaptoaniline) can be employed in solution as prepared, or otherwise after neutralization employing a mineral acid followed by extraction with ethyl ether and removal of the solvent by distillation so as to obtain 14.5 parts of a technical grade product which is a slightly yellow oil compound.

The general conditions employed in the flotatin tests are illustrated in the following examples:

Grinding: a 90 g sample drawn from an ore mined at Caitas (Sardinia) after crushing and granulating to sizes less than 3 mm was introduced into a laboratory scale rod mill together with 900 g of tap water and ground for a time sufficient to obtain a sample whose 90% was of particle size less than 100 micron, then the sample was drawn out of the mill and diluted with 3 l of water.

Cyclone processing: the sample from the grinding operation was processed in a Raffinot microcyclone having a 1.5 mm tip hole and under a pressure of 1 atmosphere. This operation allows the elimination of an ore fraction amounting to about 15% of the total weight, the 90% of which is of sizes smaller than 12 micron. The fraction whose 80% is of sizes between 10 and 100 micron was processed by flotation; material balances are referred to that fraction.

Flotation procedure: the fines-free sample coming from the cyclone processing step was introduced into a 2 l cell making part of a Humboldt-Weday flotation apparatus, and said sample was stirred by the rotor of the apparatus itself. While keeping the air inlet valve closed one of the reagents in question was added, said reagents being identified in the following by the letters DN and a digit, and said sample was kept two minutes for conditioning, then adding a reagent for the production of a froth (frothing). At the end of the conditioning time, during which the pH value was constantly controlled, the air inlet valve was opened and the speed of the rotor was adjusted at 1,200 rpm so that a froth was obtained which was reach in the ore and was removed manually by means of a pallet till exhaustion of the froth or otherwise, in case of permanence of froth, till exhaustion of the ore in the froth itself. The product of this step was pointed out in the examples as the "I product".

After the first flotation step the air valve was closed and the level of the ore pulp in the flotation cell was restored with water; then $Na_2S$ was added and the sample kept two minutes for conditioning, and a further amount of the DN reagent and of frothing reagent was added; after two more minutes for conditioning, the air inlet was opened and the operations were carried out as disclosed for the first step so as to obtain the so-called "II product". The ore remaining in the flotation cell was called the "waste".

The reagents: DN reagents in question and added as 2% water solutions;

$Na_2S$ available from the Carlo Erba added as a 2% water solution;

Aerofroth 65 frother (a frothing), available from the American Cyanamid, added as a 1% water solution;

PIN OIL N.5 (a frothing) available from the American Cyanamid added as a 1% water emulsion;

The proportion of reactants: Such proportion was given as g/tonne (i.e., as g of reactant/tonne of the solid).

Example 2

DN 46 was employed as the collecting agent, having the formula

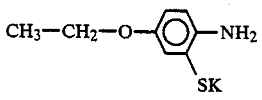

2-amino, 5-ethoxy-benzenethiol

| | | |
|---|---|---|
| I product: | DN 46 350 g/tonne | |
| | Aerofroth 65 20 g/tonne | pH 7.5 |
| II product: | $Na_2S$ 500 g/tonne | |
| | DN 46 350 g/tonne | |
| | Aerofroth 65 0 g/tonne | pH 7.8 |

Results:

| | Yield % by wt. | Concentration, % Pb | Recovery % Pb | Concentrat. % Zn | Recovery, % Zn |
|---|---|---|---|---|---|
| I product | 1.61 | 37.30 | 12.46 | 15.60 | 2.75 |
| II product | 4.19 | 57.30 | 49.82 | 5.70 | 2.62 |
| Waste | 94.20 | 1.93 | 37.72 | 9.17 | 94.63 |

Example 3

DN 47 was employed as the collecting agent having the formula

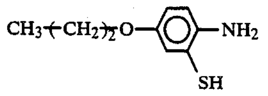

2-amino, 5n-propyl-oxybenzenethiol

| | | |
|---|---|---|
| I product: | DN 47 250 g/tonne | |
| | Pin Oil 40 g/tonne | pH 7.6 |
| II product: | $Na_2S$ 250 g/tonne | |
| | DN 47 250 g/tonne | |
| | Pin Oil 0 g/tonne | pH 7.8 |

Results:

| | Yield % by wt. | Concentration, % Pb | Recovery, % Pb | Concentrat. % Zn | Recovery, % Zn |
|---|---|---|---|---|---|
| I product | 1.04 | 43.90 | 11.00 | 16.40 | 1.96 |
| II product | 4.68 | 54.60 | 61.53 | 4.61 | 2.47 |
| Waste | 94.68 | 1.21 | 27.47 | 8.84 | 95.57 |

Example 4

DN 53 was employed as the collecting agent having the formula

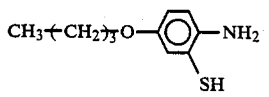

2-amino, 5n-butoxy-benzenethiol

| | | |
|---|---|---|
| I product: | DN 53 250 g/tonne | |
| | Pin Oil 40 g/tonne | pH 7.5 |
| II product: | $Na_2S$ 500 g/tonne | |
| | DN 53 500 g/tonne | |
| | Pin Oil 0 g/tonne | pH 7.8 |

Results:

| | Yield % by wt. | Concentrat. % Pb | Recovery, % Pb | Concentrat. % Zn | Recovery, % Zn |
|---|---|---|---|---|---|
| I product | 1.13 | 41.95 | 11.41 | 13.60 | 1.60 |
| II product | 5.44 | 50.00 | 65.45 | 13.20 | 7.46 |
| Waste | 93.43 | 1.03 | 23.23 | 9.37 | 92.74 |

Example 5

DN 64 was employed as the collecting agent having the formula

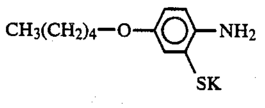

2-amino, 5n-pentyl-oxybenzenethiol

| | | |
|---|---|---|
| I product: | DN 64 1000 g/tonne | |
| | Aerofroth 65 0 g/tonne | pH 7.7 |
| II product: | $Na_2S$ 0 g/tonne | |
| | DN 64 1000 g/tonne | |
| | Aerofroth 65 20 g/tonne | pH 7.8 |

Results:

| | Yield, % by wt. | Concentrat., % Pb | Recovery, % Pb | Concentrat., % Zn | Recovery, % Zn |
|---|---|---|---|---|---|
| I product | 5.28 | 15.80 | 31.93 | 19.70 | 16.88 |
| II product | 10.94 | 13.35 | 55.88 | 18.71 | 33.22 |
| Waste | 83.78 | 0.38 | 12.19 | 3.67 | 49.90 |

Example 6

DN 65 was employed as the collecting agent having the formula

| | |
|---|---|
| 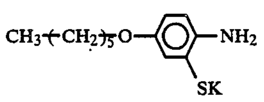 | 2-amino, 5n-hexyloxybenzenethiol |

| | | |
|---|---|---|
| I product: | DN 65 1000 g/tonne | |
| | Aerofroth 65 20 g/tonne | pH 7.5 |
| II product: | DN 65 g/tonne | |
| | $Na_2S$ 400 g/tonne | |
| | Aerofroth 65 20 g/tonne | pH 7.7 |

Results:

| | Yield % by wt. | Concen-TRAT., % Pb | Re-covery, % Pb | Concen-trat., % Zn | Re-covery, % Zn |
|---|---|---|---|---|---|
| I product | 19.85 | 5.55 | 41.13 | 18.55 | 55.95 |
| II product | 7.06 | 15.50 | 40.86 | 15.60 | 16.73 |
| Waste | 73.09 | 0.66 | 18.11 | 2.46 | 27.32 |

We claim:

1. A flotation method of separating lead or zinc values from ores containing said values comprising the steps of contacting an aqueous suspension of particles of said ores with an effective amount of an ionic organic collecting agent having the general formula

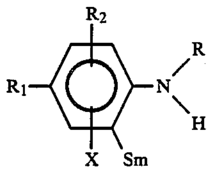

wherein:

R represents H, $CH_3$, $C_2H_5$, or an alkoxyalkyl group;

$R_1$ represents a linear alkyl, an alkoxy or a hydroxyalkyl group containing up to 12 carbon atoms;

$R_2$ represents H, a linear or a branched alkyl group, an alkoxy or a hyroxyalkyl group containing up to 12 carbon atoms;

X represents H, Cl, Br, I, F, CN, $CONH_2$, $NO_2$; and m represents H, Na, K, Li, Cs;

and separating the resulting lead or zinc enriched flotation product from the residual suspension of particles in the liquid.

2. A flotation method according to claim 1, wherein said collecting agent is 2-amino, 5-ethoxybenzenethiol.

3. A flotation method according to claim 1, wherein said collecting agent is 2-amino, 5n-propyloxybenzenthiol.

4. A flotation method according to claim 1, wherein said collecting agent is 2-amino, 5n-butoxybenzenethiol.

5. A flotation method according to claim 1, wherein said collecting agent is 2-amino, 5n-pentyloxybenzenethiol.

6. A flotation method according to claim 1, wherein said collecting agent is 2-amino, 5n-hexyloxybenzenethiol.

7. A flotation method according to claim 1 wherein in said organic collecting agent $R_2$ and X each represent hydrogen.

8. A flotation method according to claim 1, wherein in said organic collecting agent $R_1$ is an alkoxy group.

9. A flotation method according to claim 7 wherein in said organic collecting agent, $R_1$ is an alkoxy group.

* * * * *